(12) United States Patent
Park

(10) Patent No.: US 11,413,211 B2
(45) Date of Patent: Aug. 16, 2022

(54) VISION TRAINING DEVICE

(71) Applicant: EDENLUX CORPORATION, Changwon-si (KR)

(72) Inventor: Sungyong Park, Busan (KR)

(73) Assignee: EDENLUX CORPORATION, Changwon-si (KR)

(*) Notice: Subject to any disclaimer, the term of this patent is extended or adjusted under 35 U.S.C. 154(b) by 368 days.

(21) Appl. No.: 16/431,473

(22) Filed: Jun. 4, 2019

(65) Prior Publication Data

US 2019/0282434 A1    Sep. 19, 2019

Related U.S. Application Data

(63) Continuation of application No. PCT/KR2016/014645, filed on Dec. 14, 2016.

(51) Int. Cl.
*A61B 3/00* (2006.01)
*A61B 3/14* (2006.01)
(Continued)

(52) U.S. Cl.
CPC .............. *A61H 5/00* (2013.01); *A61B 3/04* (2013.01)

(58) Field of Classification Search
CPC .......... A61M 21/00; B43L 13/18; G02C 5/00; G02C 9/00; G02C 7/02; G02C 7/04; G02B 27/0103; G02B 27/145; G02B 27/144; G02B 27/0172; G02B 27/0149; G02B 27/0025; G02B 27/1013; G02B 27/126; A61H 5/00; A61B 3/103; A61B 3/14; A61B 3/113; A61B 3/1225; A61B 3/024; A61B 3/04; A61B 3/0285

USPC ... 351/203, 57, 41, 205, 206, 209, 210, 221, 351/222, 159.01, 159.74–159.76, 227, 351/234, 235; 359/13, 629–636, 618, 359/638, 640; 600/27

See application file for complete search history.

(56) References Cited

U.S. PATENT DOCUMENTS 4,408,846 A    10/1983 Balliet
4,778,268 A    10/1988 Randle
(Continued)

FOREIGN PATENT DOCUMENTS

CN    1470227 A    1/2004
CN    201356708 Y    12/2009
(Continued)

OTHER PUBLICATIONS

Office Action issued in corresponding Chinese Application No. 201680091454.1, dated Feb. 24, 2021 (8 pages).
(Continued)

*Primary Examiner* — Dawayne Pinkney
(74) *Attorney, Agent, or Firm* — Trop, Pruner & Hu, P.C.

(57) ABSTRACT

A vision training device includes a main body, a lens unit, a drive motor, and a controller. The lens unit includes a plurality of lenses respectively having different diopter values and a lens holder that supports the lenses. The drive motor moves the lens holder so that one of the lenses of the lens unit is disposed on a line of sight axis. The controller controls the drive motor such that a test lens selected from the plurality of lenses is disposed on the line of sight axis and stores an accommodation time indicating a period of time in which the eye becomes in an accommodated state to the test lens.

19 Claims, 7 Drawing Sheets

(51) Int. Cl.
*A61B 3/02* (2006.01)
*A61B 3/04* (2006.01)
*G02B 27/14* (2006.01)
*A61H 5/00* (2006.01)

(56) References Cited

U.S. PATENT DOCUMENTS

| | | | |
|---|---|---|---|
| 4,838,677 | A | 6/1989 | Bronskill et al. |
| 5,596,378 | A | 1/1997 | Kelman |
| 2003/0081175 | A1 | 5/2003 | Hosoi et al. |
| 2006/0103808 | A1 | 5/2006 | Horie |
| 2007/0038142 | A1 | 2/2007 | Todd et al. |
| 2009/0168016 | A1 | 7/2009 | Ohkawa et al. |
| 2010/0118272 | A1 | 5/2010 | Iwasaki et al. |
| 2010/0182566 | A1* | 7/2010 | Becker ................ A61B 3/0025 351/205 |
| 2012/0069296 | A1 | 3/2012 | Li et al. |
| 2017/0296421 | A1 | 10/2017 | Travers et al. |
| 2018/0032103 | A1 | 2/2018 | Eskilsson et al. |
| 2018/0263488 | A1 | 9/2018 | Pamplona et al. |

FOREIGN PATENT DOCUMENTS

| | | | |
|---|---|---|---|
| CN | 101829007 | A | 9/2010 |
| CN | 204910028 | U | 12/2015 |
| JP | H08206166 | A | 8/1996 |
| JP | H08257077 | A | 10/1996 |
| JP | H08257078 | A | 10/1996 |
| JP | H0956764 | A | 3/1997 |
| JP | H10314211 | A | 12/1998 |
| JP | H 11-032995 | | 2/1999 |
| JP | 2003-135397 | | 5/2003 |
| JP | 2004-049820 | | 2/2004 |
| JP | 2004351103 | A | 12/2004 |
| JP | 2009153658 | A | 7/2009 |
| JP | 2010088539 | A | 4/2010 |
| JP | 2010148738 | A | 7/2010 |
| JP | 2014038302 | A | 2/2014 |
| KR | 100526023 | B1 | 11/2005 |
| KR | 101370588 | B1 | 3/2014 |
| KR | 101408237 | B1 | 6/2014 |
| KR | 101490674 | | 2/2015 |
| KR | 101580477 | B1 | 12/2015 |
| KR | 1020160097858 | A | 8/2016 |
| KR | 101663765 | B1 | 10/2016 |
| KR | 10-2017545 | | 10/2019 |
| RU | 2089141 | C1 | 9/1997 |
| RU | 2144341 | C1 | 1/2000 |
| TW | 561041 | B | 11/2003 |
| WO | WO2008121087 | | 10/2008 |

OTHER PUBLICATIONS

Translation of Office Action issued in corresponding Chinese Application No. 201680091454.1, dated Feb. 24, 2021 (8 pages).
India Patent Office, Office Action dated Jul. 28, 2021 in Indian Patent Application No. 201927022472 (5 pages).
European Patent Office, Supplementary European Search Report dated Jul. 22, 2020 in European patent application No. 16924056.1, 7 pages total.
Japanese Patent Office, Notice of Allowance dated Jul. 20, 2021 in Japanese Patent Application No. 2019-529998 (6 pages).
A non-final Office action issued by the U.S. Patent Office dated Mar. 3, 2019 in connection with U.S. Appl. No. 15/281,530.
An International Search Report and Written Opinion issued by the International Searching Authority dated Jul. 28, 2017 in connection with international patent application No. PCT/KR2016/014645.
An International Preliminary Report on Patentability Chapter I issued by the International Bureau of WIPO dated Apr. 2, 2019 in connection with international patent application No. PCT/KR2017/011094.
An International Search Report and Written Opinion issued by the International Searching Authority dated Jul. 31, 2017 in connection with international patent application No. PCT/KR2016/014735.
Japanese Patent Office, Notice of Reasons for Rejection dated Dec. 22, 2020 in Japanese patent application No. 2019-529998, 9 pages total.
Notification of Registration and Notice of Granting Patent Right issued in corresponding Chinese Application No. 201680091454.1, dated Oct. 9, 2021 (5 pages).
Notification of Registration and Notice of Granting Patent Right issued in corresponding Chinese Application No. 201680091454.1, dated Feb. 24, 2021 (5 pages).

* cited by examiner

VISION TRAINING DEVICE

CROSS REFERENCE TO RELATED APPLICATION

This application is a continuation application of PCT/KR2016/014645, which was filed on Dec. 14, 2016, the entire contents of which are incorporated herein in their entirety.

BACKGROUND

The disclosure invention relates to a vision training device.

A crystalline lens adjuster muscle which affects human vision is an involuntary muscle that is not controlled by human's will. A muscular strength of the crystalline lens adjuster muscle can be enhanced through vision improvement training of causing a user to repeatedly recognize an object through lenses with different diopters. For such a training, a vision training device that automatically switches a diopter of a lens placed in front of the eye in a mechanical manner is disclosed.

In the vision training device of the related art, a method of switching a diopter lens placed in front of the eye of the user at predetermined time intervals is used. However, in the vision training device of the related art, an arbitrarily set training time is applied uniformly even though an accommodation time for a switched lens differs depending on a user. Therefore, some users feel that a lens switching time is fast, and other users feel that a lens switching time is slow, and the users have uncomfortable feeling, leading to poor training effects. Meanwhile, the accommodation time for the replaced lens indicates an accommodative facility of person vision of the user, that is, a response of a crystalline lens adjuster muscle, and a current state and a change trend thereof are important factors which should be handled with regard to vision training and performance evaluation, and they are not considered in the vision training device of the related art.

BRIEF SUMMARY

According to an aspect, a vision training device is capable of measuring and managing an accommodative status of person vision of a user.

According to an aspect, a vision training device is capable of providing vision training in which a measured accommodative status of personal vision of a user is reflected.

In an example, a vision training device includes a main body including at least one ocular hole corresponding to an eye of a user, at least one lens unit including a plurality of lenses having different diopters and a lens holder that supports the lenses with an interval therebetween and is movable with respect to the main body so that any one of the lenses is placed in a line of sight direction from the ocular hole, a drive motor that moves the lens holder, a user input unit, and a control unit that controls the drive motor such that a test lens selected from the plurality of lenses is placed in the line of sight direction and stores an accommodation time indicating a period of time in which the eye becomes an accommodated state to the test lens.

The lens holder may be rotatable on a rotation shaft with respect to the main body, and the lenses may be supported on the lens holder at a predetermined angular interval in a circumferential direction, and in this case, the lens can be switched with a relatively simple structure.

The control unit may store the accommodation time of the user for the test lens on the basis of an accommodation reflex confirmation signal input through the user input unit.

The vision training device may include a sensor module that detects the accommodated state of the eye of the user, and the control unit may store the accommodation time of the user for the test lens on the basis of an accommodation reflex confirmation signal input through the sensor module. An exemplary benefit of the vision training device is that the accommodative facility of the user vision may be measured more conveniently.

The plurality of lenses may have diopter values varying stepwise with predetermined diopter intervals therebetween, and the control unit may measure and store the accommodation time when the diopter is increased from an adjacent lens and the accommodation time when the diopter is decreased from an adjacent lens for each of the lenses. An exemplary benefit of the vision training device is that the accommodative facility of the user's vision in view of the lens switching direction may be measured more accurately.

The user input unit may include a training mode selection part, and the control unit may set a training time of each lens in which the stored accommodation time is reflected and expose a corresponding lens to a line of sight of the user during the training time corresponding to each lens when the training mode is selected through the user input unit. An exemplary benefit of the vision training device is that vision training in which the accommodative facility of the user vision is considered can be implemented.

The accommodation time of the user for the corresponding lens may be stored when the accommodation reflex confirmation signal is input through the user input unit during an operation in the training mode. An exemplary benefit of the vision training device is that vision training in which the accommodative facility of the user vision is improved and the measured results of the vision training is reflected can be implemented.

An exemplary benefit of a training device as described herein is that it is possible to provide customized vision training in which a status of personal vision of a user is considered, and thus the vision of the user can be improved more effectively through the vision training.

DETAILED DESCRIPTION

Various aspects of a vision training device and related methods according to the present disclosure are described with reference to the appended drawings. It is to be understood, however, that the following explanation is merely exemplary in describing the devices and methods of the present disclosure. Accordingly, any number of reasonable and foreseeable modifications, changes, and/or substitutions are contemplated without departing from the spirit and scope of the present disclosure.

Figure 1:
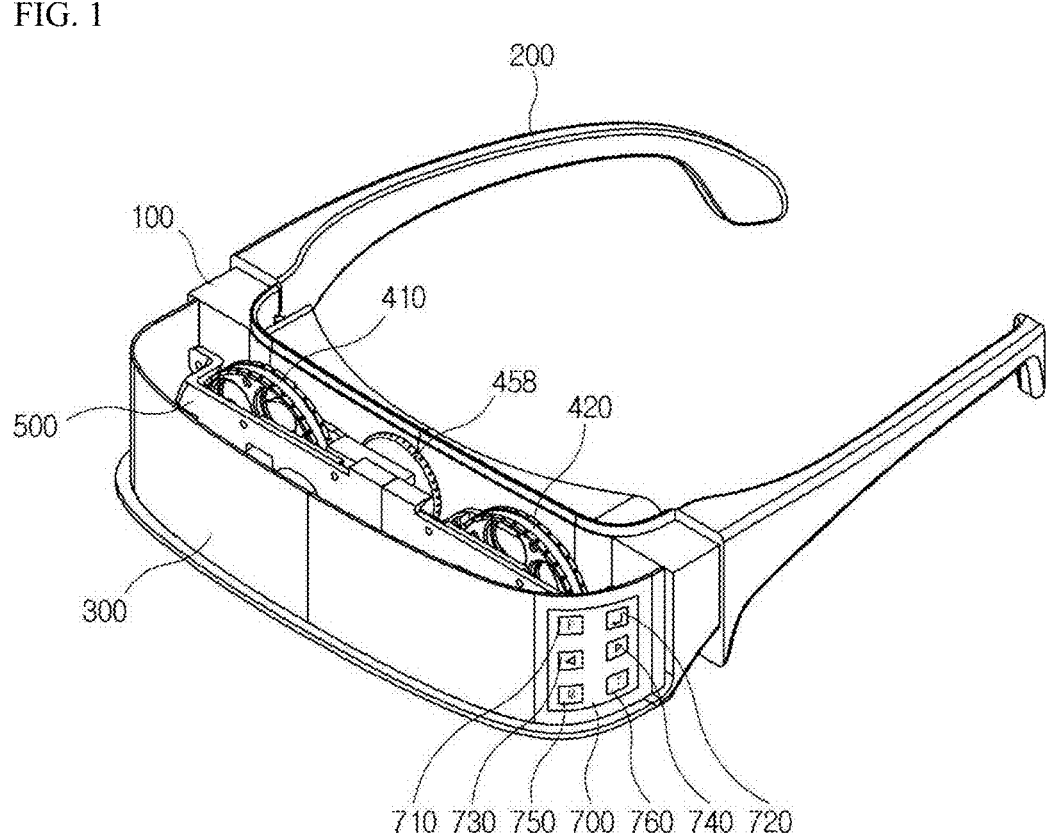
FIG. 1 is a perspective view of a vision training device in which an upper cover is removed according to an embodiment.
Figure 2:
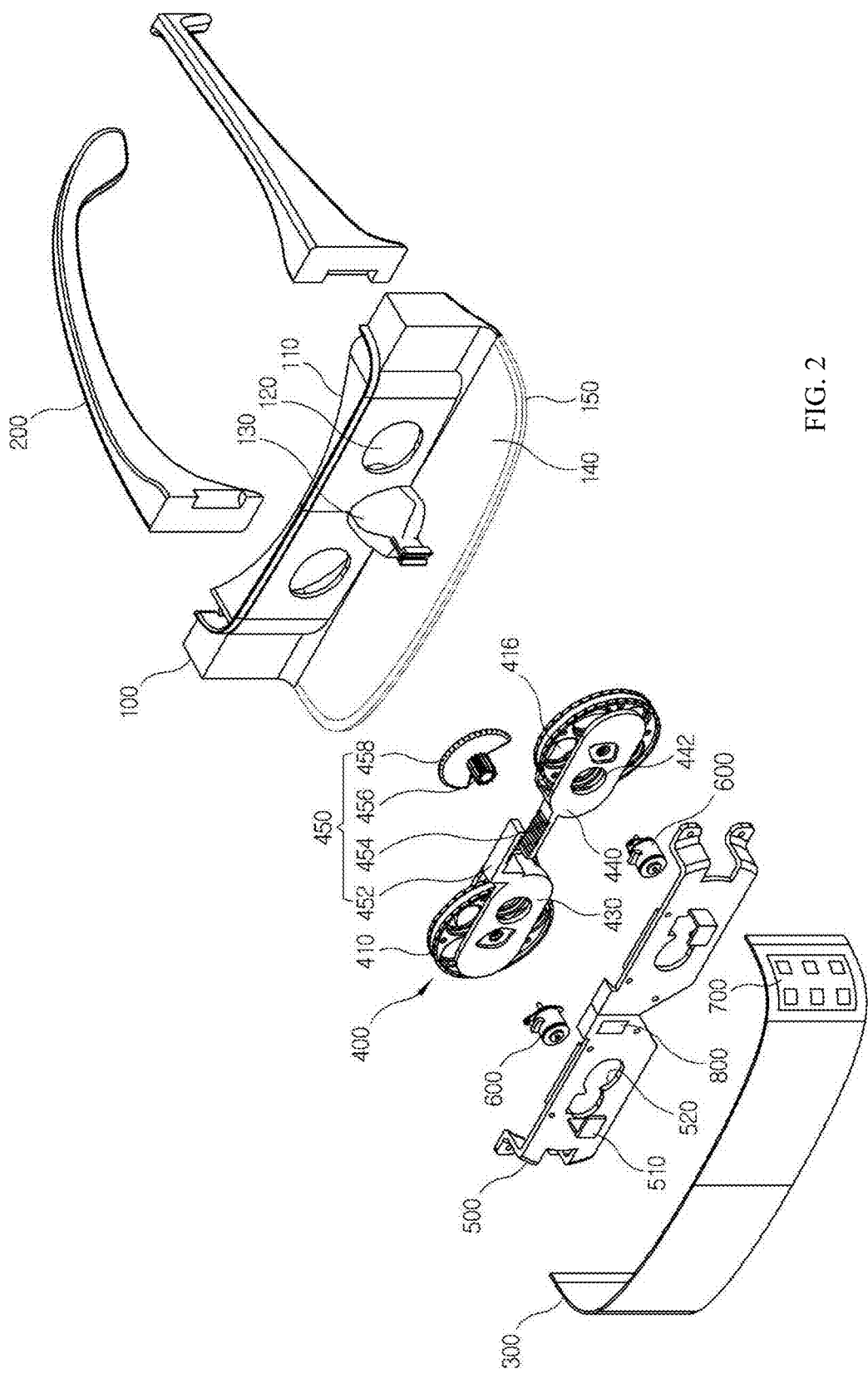
FIG. 2 is an exploded perspective view of the vision training device of FIG. 1.

FIG. 1 is a perspective view of a vision training device in which an upper cover is removed according to an embodiment, and FIG. 2 is an exploded perspective view of the vision training device of FIG. 1. Referring to FIGS. 1 and 2, a vision training device according to an embodiment includes a main body 100, temples 200 that support the main body 100 against the head so that the main body 100 can be supported on the forehead, and a front cover 300 coupled to the front surface of the main body 100. The front cover 300 has a user input unit 700 that receive various user inputs from the user. A pair of lens units 410 and 420 each including a plurality of lenses coupled thereto and a driving support unit 500 are disposed between the main body 100 and the front cover 300. The user can wear the vision training device on the head using the temples 200 similarly to glasses. The front cover 300 may be transparent such that a user wearing the vision training device may see through the cover 300 to observe a target.

The main body 100 includes a curved forehead support 110 that comes into contact with face areas around the eyes of the user, a pair of ocular holes 120 formed through the forehead support 110, a nose pad 130 that accommodates the nose of the user, a lower cover 140 that covers the lower part of the main body 100, and a front cover coupling portion 150 that is formed to protrude from the front surface of the main body 100 and couple with the front cover 300.

The forehead support 110 is formed on the back surface of the main body 100. The forehead support 110 has a shape which is curved in a direction from the rear of the main body 100 to the front of the main body 100 so that it can comfortably come into contact with the head of the user when the user wears the vision training device.

The ocular holes 120 are a pair of openings formed through the forehead support 110. The ocular holes 120 are aligned with the eyes of the user when the user wears the vision training device. The ocular holes 120 may be formed in a circular or transversely elongated oval shape.

The lower cover 140 is preferably opaque and formed in a plate shape protruding from the front surface of the main body 100, and includes the front cover coupling portion 150 which is formed on the upper surface thereof and coupled with the front cover 300.

The temples 200 have a temple shape of glasses and are coupled to the back surface of the main body 100. The temples 200 and may be replaced with a strap or a band that can support a wearing state of the vision training device.

A lens assembly 400 includes the pair of lens units 410 and 420 and a pair of shaft supports 430 and 440 supporting rotational shafts of the lens units 410 and 420. The lens assembly 400 includes an interval adjusting unit 450 for adjusting an interval or distance between the pair of lens units 410 and 420. The pair of lens units 410 and 420 have similar configurations, and the pair of shaft supports 430 and 440 have similar configurations, and for the sake of convenience of description, one of the lens units 410 and 420 and one of the shaft supports 430 and 440 will be described.

The lens unit 420 includes a lens holder that includes a plurality of lens installation holes. The lens holder may be circular and the installation holes may be arranged radially. A plurality of lenses are disposed in the plurality of lens installation holes. The lenses may have different diopter values. For example, the lenses may have diopter values that change sequentially such as −2, −1, 0, +1, and +2. The lenses may be soft or hard lenses. The lenses may be color lenses having different colors. A lens for any other purposes such as a lens to block the line of sight of the user, a polarizing lens, or a color filter may be included.

The lens unit 410 rotates by driving of a drive motor 600, so that a lens placed in a line of sight direction of the user may be switched to another lens having a diopter value different from that of the lens.

The shaft support 440 supports the rotational shaft of the lens unit 420. The shaft support 440 has front and back surfaces with which parts of the surfaces of the lens unit 420 are covered. A first opening 442 and a second opening are formed respectively on the front surface and the rear surface of the shaft support 440. The first opening 442 and the second opening are formed in the shaft portion 440 to be positioned within the line of sight direction of the user through the ocular hole 120.

The interval adjusting unit 450 includes racks 452 and 454 extending in directions facing each other from the pair of lens units 410 and 420, a pinion 456 that mesh with the racks 452 and 454, and a dial 458 that rotationally drives the pinion 456. The interval adjusting unit 450 adjusts the interval or distance between the pair of lens units 410 and 420 in accordance to a distance between the eyes depending on each user. The user may rotate the dial 458 to adjust the distance between the pair of lens units 410 and 420 in accordance with a distance between his/her eyes. The interval adjustment between the pair of lens units 410 and 420 may be performed by rotationally driving the pinion 460 by a motor.

The drive motor 600 rotates the lens units 410 and 420 under control of a control unit 800. At least one lens placed in the line of sight direction of the user is switched to a lens having a different diopter value with the rotational driving of the lens units 410 and 420. The drive motor 600 may be implemented by a DC motor but is not limited thereto. The drive motor 600 may be implemented by other motors capable of rotating the lens units 410 and 420 at a rotation angle that may be constant.

The drive motors 600 for rotating the lens units 410 and 420 are disposed in the driving unit 500. The driving support unit 500 has a drive motor coupling groove 510 in which the drive motor 600 is accommodated and a third opening 520 which is collinear with the first opening 442 of the shaft support 440.

Although the vision training device according to the embodiment of the present invention is illustrated in FIGS. 1 and 2 as including a pair of lens units, the vision training device according to the embodiment may include only one lens unit. When the vision training device includes only one lens unit, the measurement of the status of the personal vision of the user and the vision training may be performed for the left eye or the right eye using a single lens unit.

Figure 3:
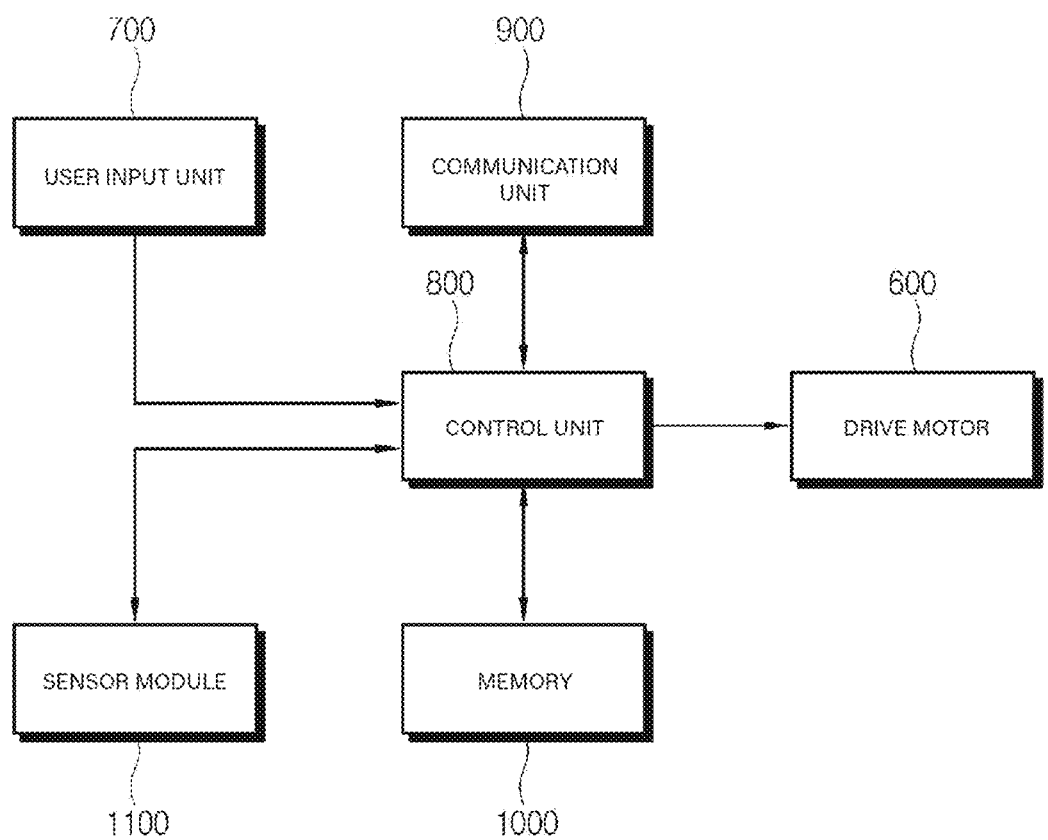
FIG. 3 is a block diagram of a vision training device according to an embodiment.

FIG. 3 is a block diagram of the vision training device according to an embodiment.

The user input unit 700 is disposed on a side of the front cover 300 of the vision training device. The user input unit 700 includes a plurality of user input buttons 710, 720, 730, 740, 750, and 760. The examples of the buttons include a power button 710, a user selection button 720, an upward button 730, a downward button 740, a measurement mode selection button 750, and a training mode selection button 760. The control unit 800 receives the user input through the user input unit 700 and controls the vision training device such that an operation corresponding to the user input is performed. The button-shaped user input unit 700 may be replaced with a keypad, a touch screen, or the like. In the illustrated embodiment, the user input unit 700 is disposed in the vision training device, but the user input unit 700 may be implemented by a wired or wireless remote controller, an application in a mobile device such as a smart phone, or the like. The user input unit 700 can be implemented by a voice recognition technique using a microphone.

A communication unit 900 performs wired or wireless communication with an external device such as a smart phone, a tablet PC, a user server, or the like. The vision training device can perform transmission and reception of data with the external device through the communication unit 900.

A memory 1000 stores user information, vision data, training data, and various types of data necessary for the operation of the vision training device. The memory 1000 causes data stored therein to be provided to the control unit 800 or the communication unit 900 or stores provided data under the control of the control unit 800.

A sensor module 1100 may be disposed at a predetermined position in the main body 100. In an example, the sensor module 1100 may output infrared light toward the eye of the user and receive infrared light reflected from the eye. The sensor module 1100 may check whether or not the eye of the user is in an accommodated state. The sensor module 1100 may check whether or not the eye of the user transitions from an accommodated state to a non-accommodated state or from the non-accommodated state to the accommodated state. The sensor module may be implemented by a principle similar to an examination principle of an auto refractor. For example, the sensor module may include a light output unit that outputs infrared light toward the eye of the user, a light detecting unit that detects reflected light reflected from the eye of the user, and a refraction evaluating unit that calculates the focal length of the detected reflected light and calculates a position at which infrared light output toward the eye focus on the eye using the focal length. The sensor module 1100 may determine that the eye of the user is in the accommodated state when the focus of the infrared light output toward the eye focuses on the retina. The sensor module 1100 may transmit an accommodation reflex confirmation signal to the control unit 800 when the eye of the user is determined to be in the accommodated state. The sensor module 1100 may transmit an accommodation state change confirmation signal to the control unit 800 when the eye of the user transitions from the accommodated state to the non-accommodated state or from the non-accommodated state to the accommodated state.

The control unit 800 performs control such that the drive motor 600 is rotationally driven at determined time intervals. The control unit 800 may adjust a rotation angle of the lens units 410 and 420 rotated by the drive motor 600. The control unit 800 may rotate the lens units 410 and 420 at a set rotation angle such that lenses placed in the line of sight direction of the user are switched to lenses having different diopters. The control unit 800 may change the rotation direction and rate of the drive motor 600.

Figure 4:
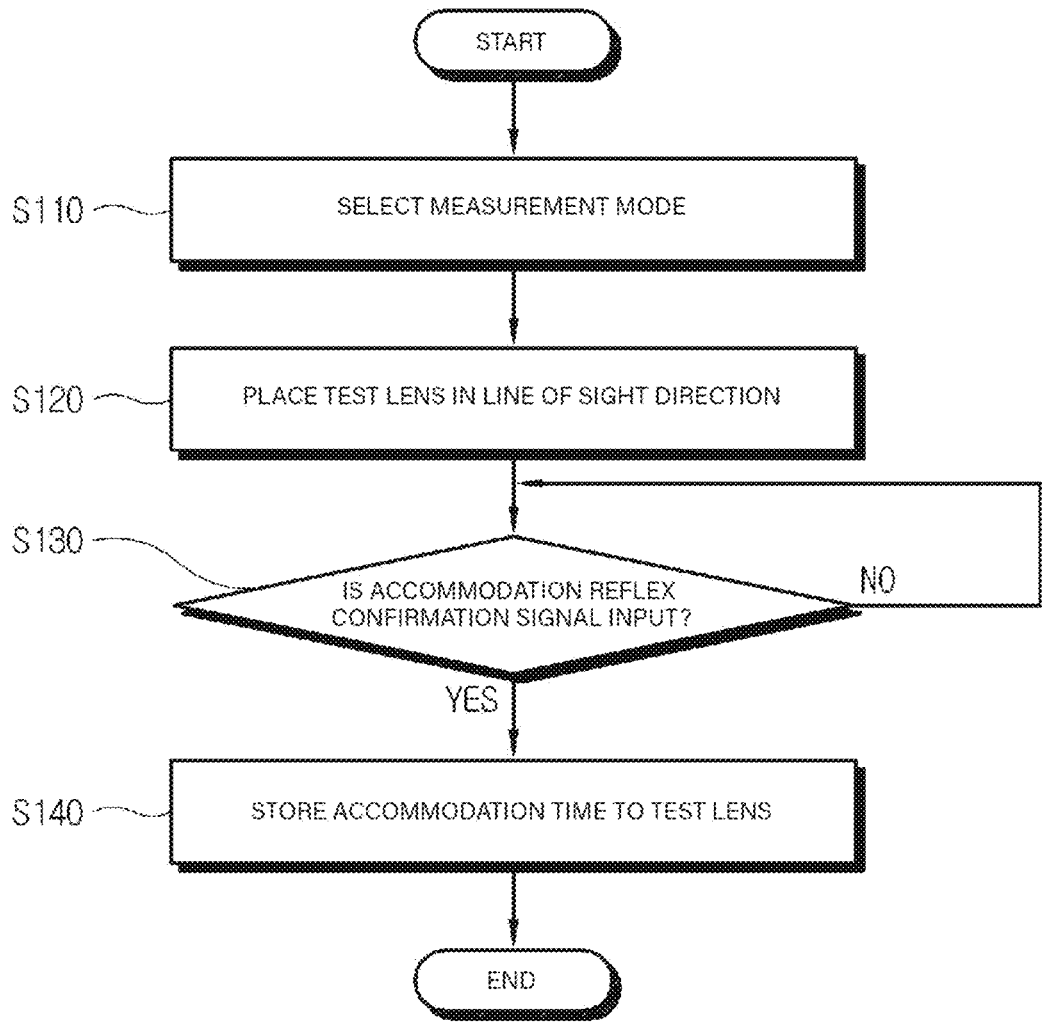
FIG. 4 is a flowchart illustrating an exemplary measurement mode operation of a vision training device according to an embodiment.
Figure 5:
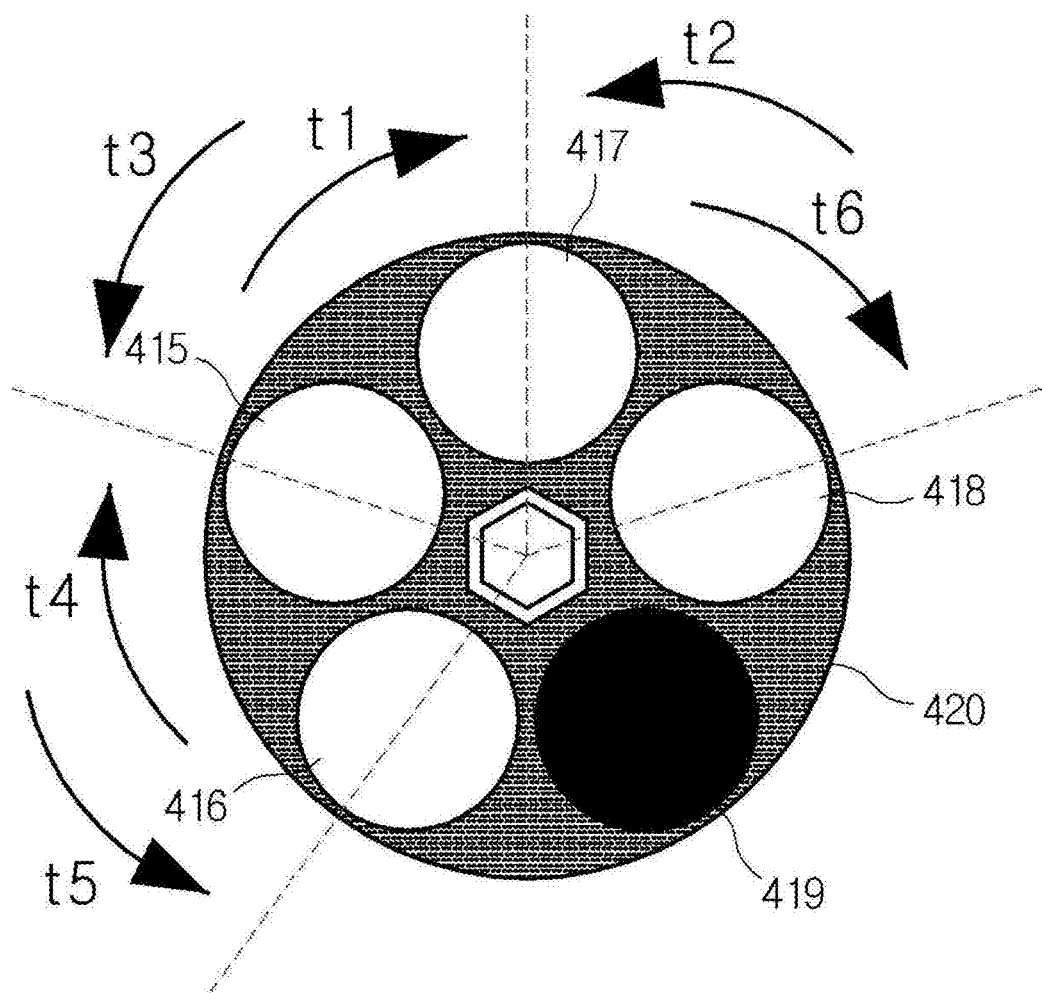
FIG. 5 is a reference diagram for describing a measurement mode operation.

FIG. 4 is a flowchart illustrating an exemplary measurement mode operation of the vision training device according to an embodiment, and FIG. 5 is a reference diagram for describing the measurement mode operation. The measurement mode operation of the vision training device according to an embodiment will be described below with reference to FIGS. 4 and 5.

The user pushes the power button 710 of the user input unit 700, so that electric power is applied to the vision training device. The user wears the vision training device and then selects the measurement mode by pushing the measurement mode selection button 750 of the user input unit 700 (S110). A target image which can be recognized by the user is arranged in front of the vision training device. The target image may be an object located at a distance, for example, a distance of 30 cm to 40 cm or an image displayed on a display of a smartphone or the like. Alternatively, the target image may be displayed on a display of the vision training device. A blocking lens 419 may be used to block the eye of the user. When the blocking lens 419 is placed in front of the eye of the user, the eye of the user is blocked so that the eye of the user does not recognize the target image. The blocking lens 419 may be used when monocular measurement or a monocular training operation is performed.

A primary lens 415 with a diopter of zero is placed in the line of sight of the user when the user uses the vision training device with an eye having correct vision or a corrected eye such as an eye wearing a contact. If the user uses the vision training device with a non-corrected eye, the user can select an arbitrary lens to be placed in the line of sight by pushing the upward button 730 or the downward button 740 of the user input unit 700. When there is an accommodation time which is already measured, the control unit 800 can select a lens with the shortest accommodation time as a lens to be placed in the line of sight of the user. This is because the lens with the short accommodation time is a lens with a diopter closest to the vision of the user.

When the user recognizes the target image through the primary lens 415, the eye of the user enters the accommodated state in which the target image is clearly recognized. When the user pushes the user selection button 720 or the up button 730 or the down button 740 in the accommodated state, the primary lens 415 is switched to a first test lens 417. The control unit 800 may cause the first test lens 417 to be exposed, for example by driving the drive motor 600, for performing the measurement mode operation to the line of sight of the user (S120). The user does not recognize the target image clearly because the lens which the eye of the user is not accommodated is placed and the eye of the user enters the non-accommodated state.

The control unit 800 checks whether or not the accommodation reflex confirmation signal is input through the user input unit 700 at step (S130). The accommodation reflex confirmation signal is a signal indicating that the user recognizes the target image through the test lens clearly. In other words, the accommodation reflex confirmation signal is a signal indicating that the eye of the user is in the accommodated state.

The accommodation reflex confirmation signal may be selectively input via the user input unit 700 or the sensor module 1100.

In the case of the input via the user input unit 700, if the user pushes the user selection button 720 of the user input unit 700 when the user recognizes the target image clearly through the first test lens 417, the accommodation reflex confirmation signal is input via the user input unit 700. In the case of the input via the sensor module 1100, the sensor module 1100 repeatedly checks whether or not the eye of the user enters the accommodated state at set intervals, and transmits the accommodation reflex confirmation signal to the control unit 800 when the eye of the user enters the accommodated state.

When the accommodation reflex confirmation signal is provided to the control unit 800, a period of time from a time at which the first test lens 417 is placed in the line of sight of the user to a time at which the accommodation reflex confirmation signal is input is stored as an accommodation time t1 for the first test lens 417.

The measurement mode operation may be performed for each of the lenses in the lens unit 420. The accommodation time for each lens is measured according to the lens switching direction. For example, when the accommodation time of the first test lens 417 is measured, the accommodation time t1 when the lens is switched to the first test lens 417 and an accommodation time t2 when the first test lens 417 is switched to a second test lens 418 are measured. This is because the accommodation time for the first test lens 417 with the same diopter value is measured, but the accommodation time may vary depending on the diopter value of the lens to which the eye of the user has already accommodated before recognizing the target image through the first test lens 417.

The accommodation times t1, t2, t3, t4, t5, and t6 for the measured lenses 415, 416, 417 and 418 are stored in the memory 1000 and used as data for training time settings.

The measurement mode described above is a mode for measuring the accommodation time of the eye of the user to the lens, and the accommodation level of the eye of the user to the lens can be used as an important parameter for evaluating the status of the personal vision of the user in association with the accommodation power of the user. With the measurement mode, it is possible to detect the status of the personal vision of the user and provide customized vision training in which the status of the personal vision is reflected, whereby the visual improvement effects can be increased.

Figure 6:
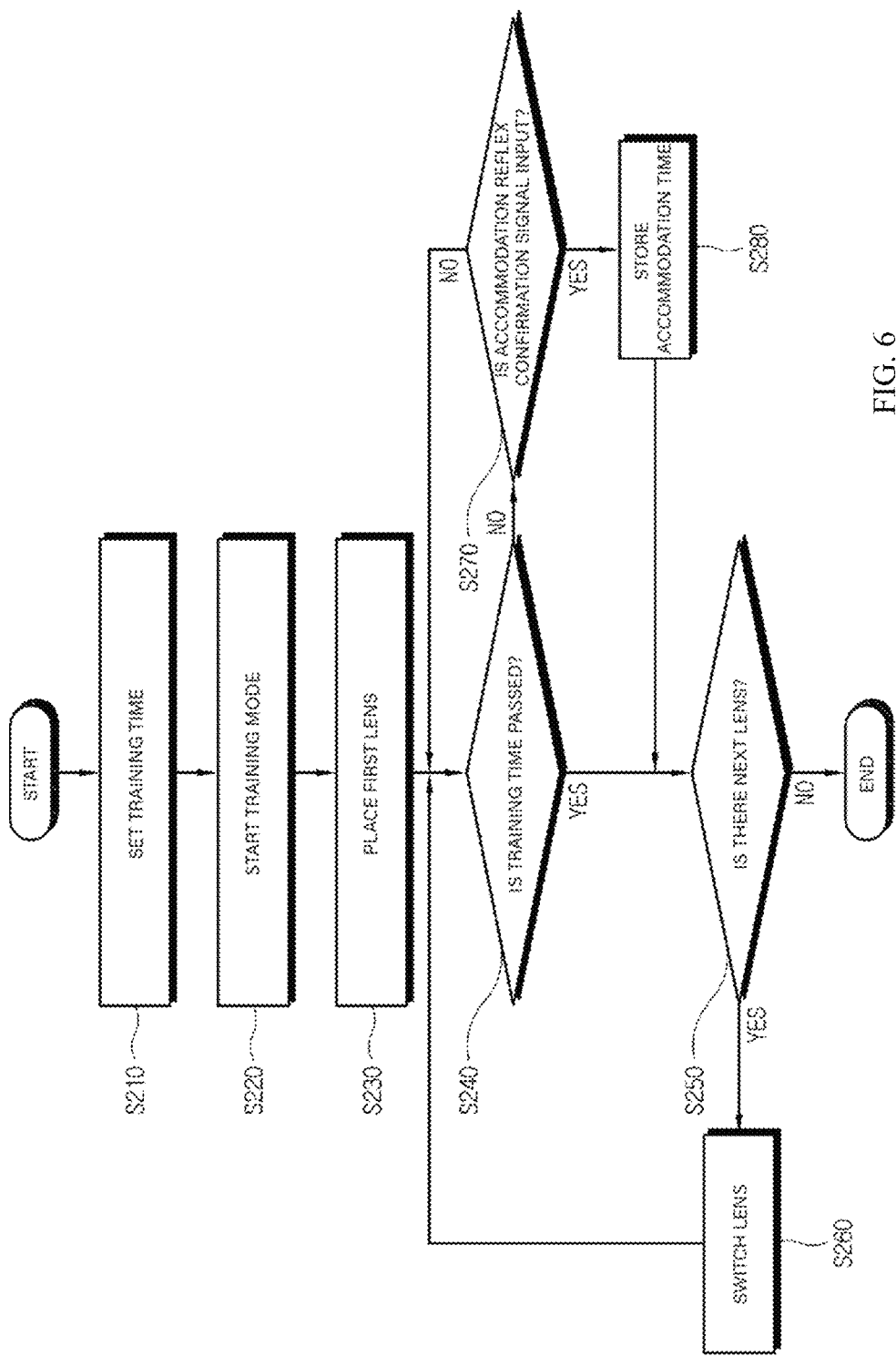
FIG. 6 is a flowchart illustrating an exemplary training mode operation of a vision training device according to an embodiment.

FIG. 6 is a flowchart illustrating an exemplary training mode operation of the vision training device according to an embodiment.

The user pushes the power button 710 of the user input unit 700, so that the electric power is applied to the vision training device. The user wears the vision training device and then selects the training mode by pushing the training mode selection button 760 of the user input unit 700.

When the training mode is selected, the control unit 800 sets a training time for each lens based on the accommodation time stored in the memory 1000 (S210) and starts the training mode operation (S220). The training time includes a period of time in which a selected lens is exposed to the line of sight of the user. An initial training time may be set to be equal to or slightly longer or shorter than the stored accommodation time. As the user repeatedly performs the vision training, the accommodation time is reduced, and the training time is reduced gradually. The vision training effects can be increased since the vision of the user is improved by the repetitive vision training.

When the user turns on the power button and selects the training mode, the control unit 800 controls the drive motor 600 such that a selected first lens among a plurality of lenses is exposed to the line of sight of the eye of the user (S230). The first lens may be a lens which is set by the user or a lens which is selected by the control unit. Preferably, the lens with the shortest accommodation time or the shortest training time is selected as the first training lens. The lens with the short accommodation time or the like is regarded as a lens with a diopter closest to the status of the person vision of the user and thus provides comfortable accommodation of the eye of the user, thereby improving the training effects.

When the training time set for the first lens is passed (S240), it is checked whether or not there is a lens which is set for the next training (S250). When there is a lens which is set for the next training, the lens selected as the first lens for training is switched to the lens set for the next training (S260).

The training process of exposing the switched lens to the line of sight of the user during the set training time is repeated. As a lens switching method, a method of automatically switching the lens in accordance with settings performed by the control unit 800 or a method of manually switching the lens in accordance with settings performed by the user via the user input unit 700 may be used. A sequential switching method in which a training start lens is set, and then the lens is sequentially switched in a clockwise or counterclockwise direction or an alternate switching method in which a pair of adjust lenses are alternately switched may be used.

The accommodation reflex confirmation signal indicating that the eye of the user has accommodated to the lens may be input during the training time for the first lens (S270). The accommodation reflex confirmation signal may be selectively input via the user input unit 700 or the sensor module 1100 as described above. When the accommodation reflex confirmation signal is input, it is that the adjuster muscle of the eye of the user has accommodated before the training time expires, and the vision of the user has accommodated to the lens earlier due to the training effects. The accommodation time may be stored (S280), the training effects of the user are evaluated, and the accommodation time is reflected when the next training time is set.

The lens switching method or a range of lenses to be switched may be set automatically by the control unit 800 or may be set manually by the user.

A sequential switching method in which a training start lens is set, and then the lens is sequentially switched in a clockwise or counterclockwise direction or an alternate switching method in which a pair of adjust lenses are alternately switched may be used.

As the range of the lenses to be switched, all the lenses may be set by the control unit 800 in a particular case, but arbitrary lenses may be selected directly by the user through the user input unit 700. Less than all of the lenses may also be selected by the control unit 800.

Through the repetition of the above-described training operation, the crystalline lens adjuster muscle of the user repeats relaxation and contraction, and as a result, the muscle strength of the crystalline lens adjuster muscle is enhanced, thereby improving the vision of the user.

The vision training device according to the embodiment of the present disclosure can provide customized vision training of measuring the accommodation response of the eye of the user to each lens in the measurement mode, setting the training conditions on the basis of the measured accommodation response, and performing the training operation, so that the vision training effects can be improved through such vision training.

Figure 7:
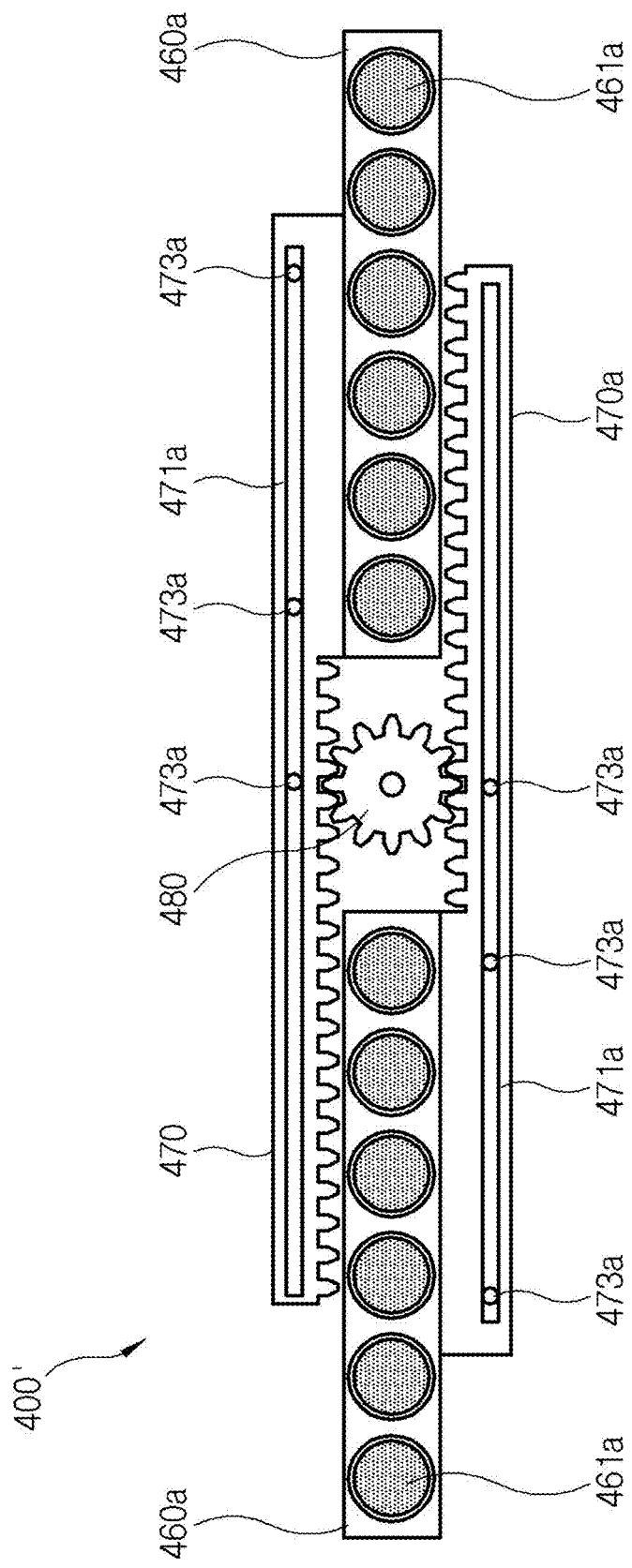
FIG. 7 is a front view of a lens holder with a sliding switching mechanism according to an embodiment.

In the above-described embodiment, the lens holder of the vision training device has been described as having a circular shape and switching the lens with the rotation, but this is not limiting. For example, the lens holder of the vision training device may have a configuration in which lenses are disposed in a line, and the lens is switched in a sliding manner. FIG. 7 is a front view illustrating a lens holder with a sliding switching mechanism.

A sliding lens assembly 400' with a sliding switching mechanism includes a pair of lens holders 460a which are configured to move in a transverse direction with an intermittent operation of the drive motor. Although the lens holder 460a is illustrated as moving in the transverse direction in FIG. 7, the lens holder 460a may be configured to move in a longitudinal direction.

The lens assembly 400' includes a lens switching driving unit 480 and rack moving units 470a disposed above and below the lens switching driving unit 480. The rack moving unit 470a has a body which extends in the transverse direction and teeth which protrude from the body toward the lens switching driving unit 480 and meshes with the lens switching driving unit 480. The pair of rack moving units 470a can be moved away from each other with clockwise rotation of the lens switching driving unit 480 or can be brought close to each other with counterclockwise rotation of the lens switching driving unit 480.

A lens holder 460a is detachably coupled to a free end side of the rack moving unit 470a. The lens holder 460a has a shape extending in the longitudinal direction of the rack moving unit 470, and a plurality of lenses 461a are disposed side by side along the longitudinal direction. Lenses 461a may be detachably installed in the lens holder 460a.

A slit 471a is formed in the rack moving unit 470a so that the rack moving unit 470a can be supported inside the main body 100 to be movable in the transverse direction. The slit 471a extends along the longitudinal direction of the rack moving unit 470a, and a plurality of support rollers 473a are inserted into the slit 471a. The support rollers 473a are fixedly installed in the main body 100 and inserted into the slit 471a to support the rack moving unit 470a so that the rack moving unit 470a is movable.

With this structure, in the lens assembly 400' with the sliding switching mechanism, the lens holders 460a can be brought away from or close to each other according to the rotation direction of the lens switching driving unit 480. As the lens holders 460a are brought away from or close to each other, the lens 461a placed in front of the eye of the user in the line of sight direction can be switched, so that the ciliary muscle of the user is enhanced.

The revolver-type lens assembly 400 and the slide-type lens assembly 400' described above may be modified in various forms depending on designs, but such modifications are included in the scope of the present disclosure.

While various embodiments in accordance with the disclosed principles have been described above, it should be understood that they have been presented by way of example only, and are not limiting.

Furthermore, the above advantages and features are provided in described embodiments, but shall not limit the application of such issued claims to processes and structures accomplishing any or all of the above advantages.

Although the invention(s) is/are described herein with reference to specific embodiments, various modifications and changes can be made without departing from the scope of the disclosure. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A vision training device, comprising:
    a main body including at least one ocular hole positioned to correspond with an eye of a user wearing the vision training device, a line of sight axis being defined to intersect with the ocular hole;
    a lens unit including a plurality of lenses respectively having different diopter values and a lens holder that supports the lenses;
    a drive motor configured to move the lens holder so that one of the lenses of the lens unit is disposed on the line of sight axis;
    a controller configured to control the drive motor such that a test lens selected from the plurality of lenses is disposed on the line of sight axis and to store an accommodation time indicating a period of time in which the eye becomes in an accommodated state to the test lens; and
    a user input unit that includes a training mode selection part;
    wherein the controller is configured to set a training time associated with each lens based at least in part on a stored accommodation time for the respective lens and cause the respective lens to be disposed on the line of sight axis during the training time when the training mode is selected through the user input unit.

2. The vision training device according to claim 1, wherein
    the lens holder is rotatably coupled to the main body by a rotation shaft, and
    the lenses are disposed on the lens holder at angular intervals along a circumference of the lens holder.

3. The vision training device according to claim 1, wherein the controller is configured to store the accommodation time for the test lens in response to an accommodation reflex confirmation signal input to a user input unit.

4. The vision training device according to claim 1, further comprising
    a sensor module configured to detect the accommodated state of the eye of the user, wherein
    the controller is configured to store the accommodation time of the user for the test lens in response to an accommodation reflex confirmation signal input from the sensor module.

5. The vision training device according to claim 1, wherein the plurality of lenses respectively have diopter values varying stepwise with a same diopter interval therebetween, and
    the controller is configured to measure and store the accommodation time when the diopter is increased from an adjacent lens and the accommodation time when the diopter is decreased from an adjacent lens.

6. The vision training device according to claim 1, wherein, in the training mode, the controller is configured to change the lens disposed on the line of sight axis after the lens is disposed on the line of sight axis for the training time for each of the plurality of lenses.

7. The vision training device according to claim 1, wherein the controller is configured to store the accommodation time of the user for a respective one of the lenses when an accommodation reflex confirmation signal is input through the user input unit during an operation in the training mode.

8. The vision training device according to claim 1, wherein:
the controller is configured to store first and second accommodation times for the test lens;
the first accommodation time is based on accommodation time after the test lens is replaced by a first lens;
the second accommodation time is based on accommodation time after the test lens is replaced by a second lens;
the first and second lens have differing diopter values from each other.

9. The vision training device according to claim 8, wherein the controller is configured to store first and second accommodation times for the test lens according to two different switching directions between the test lens and two adjacent lenses.

10. The vision training device according to claim 9, wherein the two adjacent lenses have differing diopter values from each other.

11. The vision training device according to claim 1, wherein the training time associated with each lens is unequal to the stored accommodation time for the respective lens.

12. The vision training device according to claim 11, wherein the controller is configured to decrease the training time associated with each lens in response to training the user.

13. A vision training method, comprising:
providing a vision training device having: (a)(i) a main body that includes at least one ocular hole positioned to correspond with an eye of a user wearing the vision training device, and (a)(ii) at least one controller to control a drive motor; wherein (b)(i) the vision training device is configured so that at least one of a plurality of lenses is selected and disposed along a line of sight of the user, (b)(ii) the plurality of lenses respectively have different diopter values, and (b)(iii) a line of sight axis intersects with the ocular hole;
selecting a test lens from the plurality of lenses and driving the drive motor to dispose the test lens on the line of sight axis;
storing, in a non-transitory computer readable memory, an accommodation time indicating a period of time in which an eye of the user becomes in an accommodated state to the test lens;
setting a training time associated with each lens based at least in part on a stored accommodation time for the respective lens; and
driving the drive motor to position the respective lens on the line of sight axis during the training time when a training mode is selected through a user input unit.

14. The vision training method according to claim 13, wherein
the driving includes rotating a lens holder about a rotation shaft, and
the lenses are disposed on the lens holder at angular intervals along a circumference of the lens holder.

15. The vision training method according to claim 13, wherein the storing includes storing the accommodation time for the test lens in response to an accommodation reflex confirmation signal input to the user input unit.

16. The vision training method according to claim 13, wherein the storing includes storing the accommodation time for the test lens in response to an accommodation reflex confirmation signal from a sensor module.

17. The vision training method according to claim 13, wherein
the plurality of lenses respectively have diopter values varying stepwise with a same diopter interval therebetween, and
the method includes measuring and storing the accommodation time for the respective lens when the diopter is increased from an adjacent lens and the accommodation time for the respective lens when the diopter is decreased from an adjacent lens.

18. The vision training method according to claim 13, further comprising, in the training mode, changing the lens disposed on the line of sight axis after the lens is disposed on the line of sight axis for the training time for each of the plurality of lenses.

19. The vision training method according to claim 13, further comprising storing the accommodation time of the user for a respective one of the lenses when an accommodation reflex confirmation signal is input through the user input unit during an operation in the training mode.

* * * * *